United States Patent [19]

Jancis

[11] 4,089,839
[45] May 16, 1978

[54] 5-CHLORO-2-(2'-HYDROXY-5'-TERT-OCTYLPHENYL)BENZOTRIAZOLE AND POLYPROPYLENE STABILIZED THEREWITH

[75] Inventor: Elmar Harry Jancis, Naugatuck, Conn.

[73] Assignee: Uniroyal, Inc., New York, N.Y.

[21] Appl. No.: 693,568

[22] Filed: Jun. 7, 1976

Related U.S. Application Data

[62] Division of Ser. No. 418,135, Nov. 21, 1973, Pat. No. 3,978,074.

[51] Int. Cl.$^2$ .................... C08K 5/34; C07D 249/20; C07D 401/04
[52] U.S. Cl. .................. 260/45.8 NT; 260/155; 260/156; 260/192; 260/197; 260/206; 260/288 CE; 260/296 B; 260/308 B
[58] Field of Search ............... 260/45.8 NT, 308 B

[56] References Cited

U.S. PATENT DOCUMENTS

| | | | |
|---|---|---|---|
| 3,189,615 | 6/1965 | Heller et al. | 260/308 |
| 3,230,194 | 1/1966 | Boyle | 260/45.8 |
| 3,244,667 | 4/1966 | Burgess et al. | 260/45.8 NT |
| 3,271,339 | 9/1966 | Cappuccio et al. | 260/45.8 NT |
| 3,405,089 | 10/1968 | Mauz et al. | 260/45.8 NT |
| 3,481,897 | 12/1969 | Marinaccio et al. | 260/45.8 NT |
| 3,600,355 | 8/1971 | Cyba | 260/45.8 NT |

FOREIGN PATENT DOCUMENTS

1,006,781 10/1965 United Kingdom.

Primary Examiner—H.S. Cockeram
Attorney, Agent, or Firm—James J. Long

[57] ABSTRACT

Catalytic hydrogenation of o-nitrophenylazohydroxyaryls in an alkaline medium yields hydroxyarylbenzotriazoles; under mild conditions an N-oxide is formed. E.g., 6-tert-butyl-2-(5'-chloro-2'-nitrophenylazo)-p-cresol is hydrogenated to 5-chloro-2-(3'-tert-butyl-2'-hydroxy-5'-methylphenyl)benzotriazole, using platinum sulfide catalyst in the presence of sodium hydroxide:

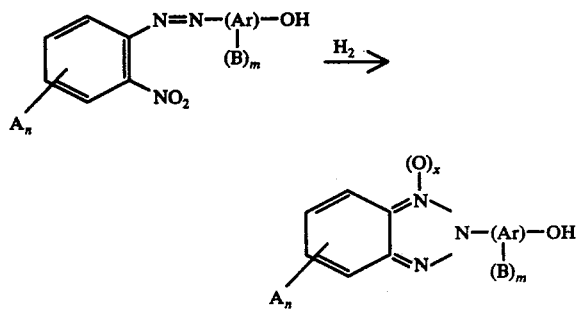

in this case A in the starting chemical is 5-chloro, $n$ is 1, Ar is a phenyl nucleus, $m$ is 2, one B is 6-tertbutyl and the other B is 4-methyl; in the product $x$ is zero. Chemicals useful for various purposes, including the stabilization of polymeric materials (e.g., polypropylene, polyvinyl chloride) against light, may be made by the process.

2 Claims, No Drawings

5-CHLORO-2-(2'-HYDROXY-5'-TERT-OCTYL-PHENYL)BENZOTRIAZOLE AND POLYPROPYLENE STABILIZED THEREWITH

This is a division of application Ser. No. 418,135, filed Nov. 21, 1973, now U.S. Pat. No. 3,978,074 issued Aug. 31, 1976.

This invention relates to a method of making hydroxyarylbenzotriazoles and their N-oxides.

2-(2'-Hydroxyphenyl)benzotriazoles are known as light stabilizers for plastics (U.S. Pat. No. 3,004,896, Heller et al., Oct. 17, 1961). One method of making these compounds involves reducing an azo compound with powdered zinc (U.S. Pat. No. 3,214,436, Boyle et al., Oct. 26, 1965) but this method presents a problem of separation of large amounts of zinc oxide from the product. Another method involves oxidizing a diaminohydroxyazobenzene to form a 5-amino-2-(2'-hydroxyphenyl)benzotriazole which must then be subjected to an undesirable diazotization step. It would be desirable to use the cheapest and most convenient reducing agent, hydrogen gas, but, unfortunately, instead of the desired benzotriazole, the usual products of catalytic hydrogenation of a nitrophenylazophenol are the corresponding o-phenylenediamine and o-aminophenol in nearly quantitative yield [W. F. Whitmore and A. J. Revukus, J. Am. Chem. Soc., 62, 1687 (1940)]. The present invention is based on the surprising discovery that in an alkaline medium, the catalytic hydrogenation does not produce the previously observed cleavage of azobenzene N=N bond but instead yields the desired 2-(hydroxyphenyl)benzotriazole.

U.S. Pat. No. 3,197,475, Carboni, July 27, 1965, discloses catalytic hydrogenation of the benzene ring of certain benzotriazoles to yield tetrahydrobenzotriazoles. From such a teaching, it is unexpected that the present catalytic hydrogenation stops at the benzotriazole. There is no disclosure of hydrogenation of compounds with an azobenzene N=N double bond.

In accordance with the invention an hydroxyarylbenzotriazole or N-oxide thereof is prepared by catalytically hydrogenating an o-nitrophenylazohydroxyaryl compound in an alkaline medium. A surprising feature of the process is that, in the alkaline medium employed, the catalytic hydrogenation does not produce the previously observed cleavage of the azobenzene N=N bond.

When the catalytic hydrogenation of the o-nitrophenylazohydroxyaryl compound in alkaline medium is continued until two moles of hydrogen have been absorbed (in addition to any hydrogen used up by side reactions), the product is the benzotriazole itself. When the reaction is stopped after absorption of only one mole of hydrogen, the benzotriazole N-oxide (1-oxide) may be obtained. Thus, the invention enables the production, selectively, of the benzotriazole or its N-oxide, depending upon the severity of the hydrogenation conditions, as will be made manifest in the working examples below.

The catalytic hydrogenation process of the invention is carried out under alkaline conditions in a liquid solvent medium which may be either aqueous or non-aqueous. Water is the preferred solvent medium, but a non-aqueous polar organic solvent liquid such as an alkanol (e.g., a $C_1$–$C_4$ alkanol) may also be used, or a mixture of polar solvents, such as water and an alkanol, may be used. Most likely the actual species reduced is not the nitrophenyl-azophenol itself but its corresponding anion.

To provide the required alkaline conditions for carrying out the hydrogenation, various bases may be used, such as alkali metal hydroxides (e.g., sodium hydroxide, potassium hydroxide, lithium hydroxide, magnesium hydroxide, calcium hydroxide) and the like. For best results at least a molar amount of base is used, that is, at least one mole of base per mole of starting o-nitrophenylazohydroxyaryl compound. The starting o-nitrophenylazohydroxyaryl compound is at least partially soluble in the solvent medium containing such base.

Any conventional hydrogenation catalyst may be employed in the invention. Typical hydrogenation catalysts are the platinum metals, that is, noble metals of Group VIII (platinum, palladium, iridium, osmium, rhodium and ruthenium), and other metals such as nickel, cobalt, molybdenum, etc., either in the form of the metal itself or compounds thereof, such as oxides, sulfides, and the like. The catalyst may be employed in an unsupported state or it may be supported on a suitable conventional carrier, such as charcoal, kieselguhr, alumina, silica, clay, or the like.

In many cases the hydrogenation process of the invention is carried out at a temperature within the range of from 15° C to 100° C, under a pressure of from atmospheric pressure to 1000 psig or more. Under mild conditions (low temperature and pressure, short reaction time), with absorption of only one mole of hydrogen, an N-oxide is obtainable while more severe conditions (high temperature and pressure, longer reaction time) absorption of two moles of hydrogen with formation of the benzotriazole itself is favored.

In certain cases the type of product obtained is influenced by catalyst selection. Thus, the more active catalysts, which operate readily at lower reaction temperatures, are especially useful for the production of N-oxides, while the less active catalysts are usually employed at higher reaction temperatures to produce the benzotriazole itself.

Furthermore, if the starting compound contains a halogen substituent, use of a sulfide catalyst will favor retention of the halogen in the final product [see F. S. Dovell and H. Greenfield, J. Am. Chem. Soc., 87, 2767 (1965)]. On the other hand, if it is desired to remove the halogen, use of catalysts other than sulfides, such as nickel or the noble metals, will promote the removal of halogen; thus, on reduction of the halogen-containing nitrophenylazophenol, a benzotriazole may be obtained that contains no halogen. Such removal of halogen permits one to make 2-(2'-hydroxyphenyl)benzotriazoles that have a free 5' position. These are compounds that are otherwise difficult to make by conventional methods.

It will be understood that the starting compound may be substituted with any desired moieties, including essentially inert moieties, or moieties which can be hydrogenated under the reaction conditions (e.g., nitro, nitroso, or olefinic substituents), in which case the moiety will of course appear in the product in reduced form (and, of course, proportionately more hydrogen will be consumed).

In the starting o-nitrophenylazohydroxyaryl compound the aryl moiety is typically phenyl, although any other aryl group is suitable, including those having up to 18 carbon atoms, e.g., naphthyl, anthryl, acenaphthyl, etc., and equivalent heterocyclics such s pyridyl, quinolyl, and the like. The hydroxyl group may be in various positions on the aryl nucleus, e.g., 2-position, 4-position, etc.

It will accordingly be understood that the synthetic method of the invention is general to all o-nitrophenylhydroxyaryls. Thus, the starting o-nitrophenylazohydroxyaryl compound may be unsubstituted, or may carry any substituent or substituents desired. Such substituents may be either on the phenyl nucleus of the o-nitrophenyl moiety, or on the aryl nucleus of the hydroxyaryl moiety, or both, in any available position. There may be 1, 2, 3, 4 or more such substituents, which can be the same or different and in some cases can be linked together to form cyclic structures. Among the substituents there may be mentioned by way of non-limiting example such bodies as halogen (e.g., chlorine, bromine), alkyl (whether lower alkyl as in methyl, ethyl, etc., or higher alkyl as in dodecyl, stearyl, etc., whether primary secondary or tertiary [e.g., sec-butyl, tert-amyl]), alkoxy (e.g., methoxy, ethoxy, butoxy, hexoxy, dodecoxy, etc.), aryl (e.g., phenyl, naphthyl, biphenyl, anthracenyl, etc.), aralkyl (e.g., benzyl, phenethyl, trityl, etc.), alkaryl (e.g., tolyl, ethylphenyl, xylyl, etc.), aryloxy (e.g., phenoxy, naphthoxy, etc.), cycloalkyl (e.g., cyclopentyl, cyclohexyl, cyclooctyl, etc.), alkyloxyalkyl (e.g., methoxyethyl, butyloxymethyl, etc.), aryloxy alkyl (e.g., phenoxymethyl, phenoxypropyl, etc.), hydroxy alkyl (e.g., hydroxyethyl, hydroxypropyl), alkyl thio (e.g., methylthio, butylthio), arylthio (e.g., phenylthio), alkyl sulfonyl (e.g., methylsulfonyl), aryl sulfonyl (e.g., phenylsulfonyl), alkyl sulfinyl (e.g., ethylsulfinyl), aryl sulfinyl (e.g., phenylsulfinyl, tolylsulfinyl), alkyl amino (e.g., butylamino), aryl amino (e.g., phenylamino, tolylamino), dialkyl amino (e.g., dimethylamino), diaryl amino (e.g., diphenylamino) alkylarylamino (e.g., ethylphenylamino), arkyl amino alkyl (e.g., methylaminoethyl), dialkylamino alkyl (e.g., dimethylaminoethyl), halo-alkyl (e.g., chloroethyl), nitro, nitroso, cyano, alkenyl (e.g., allyl), cyclo alkenyl (e.g., cyclopentenyl), alkyl amido (e.g., acetamido), cyclo alkyl amido (e.g. cyclohexylamido) alkenylmido (e.g., acrylamido), alkimido (e.g. acetimido), carbamyl, alkylcarbamyl (e.g., alanyl), aryl carbamyl (e.g., phenylcarbamyl), dialkyl carbamyl (e.g., dimethylcarbamyl), carboalkoxy (e.g., carbethoxy), carboaryloxy (e.g., carbophenoxy), carboalkoxy alkyl (e.g., carbethoxymethyl), carboaryloxy alkyl (e.g., carbophenoxymethyl), carboxy alkyl (e.g., carboxymethyl), glycolyl, glycyl, aroyl (e.g., benzoyl), alkoyl (e.g., butyryl, acetyl) alkenoyl (e.g., acrylyl), and the like.

Representative starting chemicals include 2-(5'-chloro-2'-nitrophenylazo)-6-tert-butyl-p-cresol, 2-(4'-methoxy-2'-nitrophenylazo)-4-phenylphenol, 2-(4'-phenoxy-2'-nitrophenylazo)-4-cyclohexylphenol, 2-(2'-nitro-4'-phenylsulfonylphenylazo)-4-methoxyethylphenol, 2-(2',4'-dinitrophenylazo)-5-butylaminophenol, 2-(4'-methylsulfinyl-2'-nitrophenylazo)-4-benzylphenol, 2-(2'-nitrophenylazo)-4-dimethylaminophenol, 2-(4'-tolyl-2'-nitrophenylazo)-4-hydroxyethylphenol, 4-(2'-nitrophenylazo)phenol, 2-(2'-nitrophenylazo)-4-diphenylaminophenol, 2-(2'-nitrophenylazo)-4-phenoxyethylphenol, 2-(2'-nitrophenylazo)-4-methylthiophenol, 2-(4'-phenylthio-2'-nitrophenylazo)-4-dimethylaminoethylphenol, 2-(4'-methylsulfonyl-2'-nitrophenylazo)-4-phenylaminophenol, 2-(4'-phenylsulfinyl-2'-nitrophenylazo)-4-phenylcarbamylphenol, 2(4'-chloroethyl-2'40 -nitrophenylazo)-4-(N-ethyl-N-p-tolylamino)phenol, 2-(4'-benzoyl-2'-nitrophenylazo)-4-carbethoxyphenol, 4-(4'-nitroso-2'-nitrophenylazo)-2-carbophenoxyphenol, 4-(4'-cyano-2'-nitrophenylazo)-2-methylaminoethylphenol, 2-(2'-nitrophenylazo)-5-acetamido-4-propenylphenol, 2-(2'-nitrophenylazo)-5-cyclohexylamido-4-cyclopentenylphenol, 2-(2'-nitrophenylazo)-4-acetamidophenol, 2-(4'-bromo-2'-nitrophenylazo)-4-carbamylphenol, 2-(2'-nitrophenylazo)-4-alanylphenol, 2-(2'-nitrophenylazo)-4-dimethylcarbamylphenol, 2-(2'-nitrophenylazo)-4-carbethoxymethylphenol, 2-(2'-nitrophenylazo)-4-carbophenoxymethylphenol, 2-(2'-nitrophenylazo)-4-carboxymethylphenol, 2-(2'-nitrophenylazo)-4-glycolyphenol, 2-(2'-nitrophenylazo)-4-glycylphenol, 2-(2'-nitrophenylazo)-4-butyrylphenol, 2-(2'-nitrophenylazo)-4-acrylylphenol, 6-(2'-nitrophenylazo)-3-hydroxypyridine, 5-(2'-nitrophenylazo)-8-hydroxyquinoline, 1-(4'-chloro-2'-nitrophenylazo)-2-naphthol, 4-(2'-nitrophenylazo)-1-anthrol, and the like.

By the hydrogenation method of the invention, o-nitrophenylazohydroxyaryl compounds such as the foregoing are converted into the corresponding hydroxyarylbenzotriazoles, or their N-oxides, such as 5-chloro-2-(2'-hydroxy-3'-tert-butyl-5'-methylphenyl)-benzotriazole, 5-methoxy-2-(2'-hydroxy-5'-phenylphenyl)benzotriazole, 5-phenoxy-2-(2'-hydroxy-5'-cyclohexylphenyl)benzotriazole-N-oxide, 5-phenylsulfonyl-2-(2'-hydroxy-5'-methoxyphenyl)benzotriazole, 5-amino-2-(2'-hydroxy-4'-butylaminophenyl)benzotriazole, 5-methylsulfinyl-2-(2'-hydroxy-5'-benzylphenyl)benzotriazole, 2-(2'-hydroxy-5'-dimethylaminophenyl)benzotriazole-N-oxide, 5-tolyl-2-(2'-hydroxy-5'-hydroxyethylphenyl)benzotriazole, 2-(4'-hydroxyphenyl)benzotriazole, 2-(2'-hydroxy-5'-diphenylaminophenyl)benzotriazole, 2-(2'-hydroxy-5'-phenoxyethylphenyl)benzotriazole-N-oxide, 2-(2'-hydroxy-5'-methylthiophenyl)benzotriazole, 5-phenylthio-2-(2'-hydroxy-5'-dimethylaminoethylphenyl)benzotriazole, 5-methylsulfonyl-2-(2'-hydroxy-5'-phenylaminophenyl)benzotriazole, 5-phenylsulfinyl-2-(2'-hydroxy-5'-phenylcarbamylphenyl)benzotriazole, 5-ethyl-2-(2'-hydroxy-5'-N-ethyl-N-tolylaminophenyl)benzotriazole, 5-benzoyl-2-(2'-hydroxy-5'-carbethoxyphenyl)benzotriazole, 5-amino-2-(4'-hydroxy-3'-carbophenoxyphenyl)benzotriazole, 5-cyano-2-(4'-hydroxy-3'-methylaminoethylphenyl)benzotriazole, 2-(2'-hydroxy-4'-acetamido-5'-propylphenyl)benzotriazole, 2-(2'-hydroxy-4'-cyclohexylamido-5'-cyclopentylphenyl)-benzotriazole, 2-(2'-hydroxy-5'-acetamidophenyl)benzotriazole, 2-(2'-hydroxy-5'-carbamylphenyl)benzotriazole, 2-(2'-hydroxy-5'-alanylphenyl)benzotriazole, 2-(2'-hydroxy-5'-dimethylcarbamylphenyl)benzotriazole, 2-(2'-hydroxy-5'-carbethoxymethylphenyl)benzotriazole, 2-(2'-hydroxy-5'-carbophenoxymethylphenyl)benzotriazole, 2-(2'-hydroxy-5'-carboxymethylphenyl)benzotriazole, 2-(2'-hydroxy-5'-glycolylphenyl)benzotriazole, 2-(2'-hydroxy-5'-glycylphenyl)benzotriazole, 2-(2'-hydroxy-5'-butyrylphenyl)benzotriazole-N-oxide, 2-(2'-hydroxy-5'-propionylphenyl)benzotriazole, 3-hydroxy-6-(2'-benzotriazolyl)pyridine, 5-(2'-benzotriazolyl-8-hydroxyquinoline, 5-chloro-2-(2'-hydroxy-1-naphthyl)benzotriazole, 2-(4'-hydroxyanthryl)benzotriazole, and the like.

In one form of the invention any hydrogenation catalyst is employed to incorporate two moles of hydrogen into a halogen-free o-nitrophenylazohydroxyaryl compound to convert it to the corresponding hydroxyarylbenzotriazole (such two moles of hydrogen of course being in addition to any hydrogen consumed by hydrogenatable substituents that might be present in the o-nitrophenylazohydroxyaryl starting compound).

In another form of the invention, any hydrogenation catalyst other than a metal sulfide (such as a metal, a metal oxide, or other metal compound) is employed, suitably under mild conditions, to incorporate one mole of hydrogen into a halogen-free o-nitrophenylazohydroxyaryl compound and thereby convert it into the N-oxide of the corresponding hydroxyarylbenzotriazole.

Still another form of the invention involves the hydrogenation, with a metal sulfide catalyst, of an o-nitrophenylazohydroxyaryl compound substituted with at least one halogen atom (either on the nitrophenyl nucleus, or on the hydroxyaryl nucleus, or both), with absorption of two moles of hydrogen, the halogen being retained in the hydroxyarylbenzotriazole product.

Yet another form of the invention utilizes a hydrogenation catalyst other than a metal sulfide (such as a metal, metal oxide, or other metal compound) to incorporate two moles of hydrogen into an o-nitrophenylazohydroxyaryl compound substituted with at least one halogen atom (either on the nitrophenyl nucleus, or on the hydroxyaryl nucleus, or both), the halogen in this case being eliminated in the course of the hydrogenation to yield a halogen-free hydroxyarylbenzotriazole.

The foregoing reactions may be represented as follows:

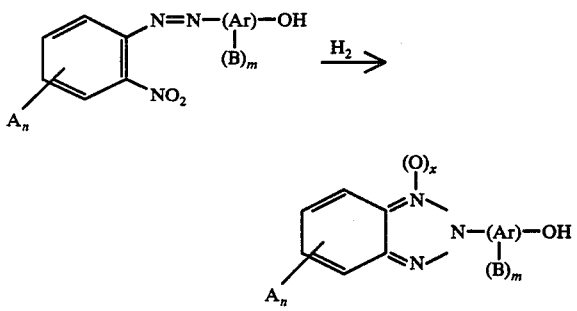

wherein Ar is an aryl moiety, A and B are hydrogen or other substituent, $n$ and $m$ are the numbers of such substituents, and $x$ is zero or 1. When there is more than one A or B substituent they may be the same or different. When any of the A's or B's are halogen, $n$ and $m$ in the product may be reduced by a number corresponding to the number of halogens eliminated.

The following examples will serve to illustrate the practice of the invention in more detail.

EXAMPLE 1

Into a Parr hydrogenation apparatus are charged 12.7 g (0.05 mole) 2-(2'-nitrophenylazo)-p-cresol, 22 ml 6N sodium hydroxide (0.132 mole), 100 ml water and 0.3 g 5% palladium on charcoal as hydrogenation catalyst. Hydrogen gas is introduced at room temperature and 50 psig for one hour. The catalyst is filtered off. The filtrate is acidifed. A yellow precipitate (11 g, 92.5% yield, mp 129°–135°) forms. After recrystallization from ethanol the pure (mp 139°–140°) 2-(2'-hydroxy-5'-methylphenyl)benzotriazole-1-oxide is obtained.

Hydrogenation using platinum on charcoal as the catalyst gives the same product in comparable yields.

EXAMPLE 2

Into a 600 ml Magne-Drive autoclave are charged 21.5 g (0.084 mole) 2-(2'-nitrophenylazo)-p-cresol, 15 ml 6N sodium hydroxide, 195 ml water and 3.5 g 50% nickel on kieselguhr. The mixture is hydrogenated 3¾ hours at 85° and 390–510 psig. The catalyst is filtered off and washed well with dilute base. The filtrates are combined and acidified with dilute hydrochloric acid. The resulting nearly white precipitate is filtered off. A 13.2 g (70%) yield of 2-(2'-benzotriazolyl)-p-cresol is obtained (mp 118°–126°). After trituration with ethanol the mp rises to 127°–129°.

Similar results are obtained under milder conditions using supported platinum or palladium as catalysts. The product is found to be identical to the commercial product named above in this example which is also known as 2-(2'-hydroxy-5'-methylphenyl)benzotriazole.

EXAMPLE 3

Into a Parr apparatus are charged 14.7 g (0.05 mole) 1-(2'-nitrophenylazo-2-naphthol, 30 ml 6N sodium hydroxide, 100 ml ethanol and 0.3 g 5% palladium on charcoal. The mixture is hydrogenated at 50 psig and room temperature for 2 hours and about 50° overnight. The catalyst is filtered off and the filtrate is neutralized with dilute hydrochloric acid. The gummy prouct (mp 75°–105°) obtained on pouring the neutral filtrate into 400 ml water is purified by passing it through a silica column. The yield of pure (mp 142°–143°) product is 6.5 g (50%). Anal. Calcd. for 1-(2'-benzotriazolyl)-2-naphthol: C, 73.55; H, 4.24; N, 16.08. Found: C, 73.33; H, 4.18; N, 16.11.

EXAMPLE 4

Into a Parr apparatus are charged 18.2 g (0.075 mole) 4-(2'-nitrophenylazo)phenol, 20 ml 6N sodium hydroxide, 80 ml water and 0.3 g 5% palladium on charcoal. The mixture is hydrogenated at room temperature and 50 psig for 5 hours. The catalyst is filtered off, the filtrate is acidified and the precipitated product is filtered off. Thin layer chromatograph shows this product to be impure and therefore it is recharged into the Parr shaker along with 15 ml 6N sodium hydroxide, 80 ml water, and 0.3 g 5% palladium on charcoal. It is hydrogenated at elevated temperatures (ca. 60°) and 50 psig pressure for 4 hours. The catalyst is again filtered off, the filtrte acidified and the product filtered. The product (10.5 g, 66.5% yield) is pure (mp 210°–213°) 2-(4'-hydroxyphenyl)benzotriazole.

EXAMPLE 5

Into an autoclave are changed 62.5 g (0.18 mole) 6-tert-butyl-2-(5'-chloro-2'-nitrophenylazo)-p-cresol, 30 ml 6N sodium hydroxide, 90 ml water, 120 ml ethanol and 3.0 g 5% platinum sulfide on charcoal. The mixture is hydrogenated 3 hours at 28°–30° and 410–600 psig. The resulting crystalline compound is filtered off along with the catalyst. The product is taken up in chloroform, the catalyst filtered off and the chloroform evaporated. The residue (46 g, 82% yield, mp 137°–139°) is 5-chloro-2-(3'-tert-butyl-2'-hydroxy-5'-methylphenyl)-benzotriazole. It is found to be identical to the commercially available material.

EXAMPLE 6

Into a Parr apparatus are charged 11.1 g (0.4 mole) 4-chloro-2-(2'-nitrophenylazo)phenol, 80 ml water, 20 ml 6N sodium hydroxide, and 0.3 g 5% palladium on charcoal. The mixture is hydrogenated at 50 psig for 2 hours at room temperature and for 5½ hours at about 60°. After cooling, the catalyst is filtered off, the filtrate is acidifed and the resulting white precipitate (5.0 g, 60% yield, mp 118°–125°) is filtered off. After recrystallization from benzene/hexane the product, namely, 2-(2'-hydroxyphenyl) benzotriazole, melts at 124°–126°.

EXAMPLE 7

Into a 1 liter Magne-Drive autoclave are charged 25.5 g (0.091 mole) 4-chloro-2-(2'-nitrophenylazo)phenol, 15 ml 6N sodium hydroxide, 260 ml water and 3.0 g 5% platinum sulfide on charcoal. The mixture is hydrogenated 3½ hours at room temperature and 410–500 psig. The catalyst is filtered off. The filtrate is acidified and the resulting precipitate is filtered off and washed with water. A yield of 10 g (46%) of 2-benzotriazolyl-4-chlorophenol is obtained (mp 144°–147°). After recrystallization from hexane the product melts at 148°–149°. Anal. Calcd.: C, 58.67; H, 3.28; N, 17.10; Cl, 14.43. Found: C, 58.52; H, 3.21; N, 17.21; Cl, 14.68.

EXAMPLE 8

Into a 1 liter Magne-Drive autoclave are charged 6.8 g (0.021 mole) 4-bromo-2-(2'-nitrophenylazo)phenol, 4 ml 6N sodium hydroxide, 285 ml water and 3.0 g 5% platinum sulfide on charcoal. The mixture is hydrogenated 1 hour at 40°–50° and 1½ hours at 50° and 620–635 psig. The catalyst is filtered off, the filtrate is acidified with dilute sulfuric acid, and the precipitated product is filtered off and washed well with water. A 1.3 g yield (21%) of crude (mp 133°–137°) product is obtained. An aliquot is recrystallized to give 2-benzotriazolyl-4-bromophenol melting at 141°–143°. The I.R. spectrum of this compound is almost identical to that of the chloro compound prepared in Example 7.

EXAMPLE 9

This example illustrates the use of the present method of reductively cyclizing the o-nitrophenylazohydroxyaryl compound where the aryl group is a heterocyclic group.

Into a Parr hydrogenation apparatus are charged 12.2 g (0.05 mole) 2-(2'-nitrophenylazo)-5-hydroxypyridine, 20 ml 6N sodium hydroxide, 100 ml water and 0.25 g 5% palladium on charcoal. The mixture is hydrogenated at room temperature and 50 psig for 1 hour. The catalyst is filtered off. The filtrate is acidified. A brown oil separates which quickly sets into a tan solid (wt. 10 g; 88% yield). On recrystallization from ethanol the 2-(5'-hydroxy-2'-pyridyl)benzotriazole-N-oxide melts at 188°–192° C. Anal. Calcd.: C, 57.9; H, 3.53. Found: C, 58.1; H, 3.57.

EXAMPLE 10

Into a one 1 Magne-Drive autoclave are charged 54 g (0.15 mole) 2-(2'-nitrophenyl azo)-4-tert-octylphenol, 30 ml 6N sodium hydroxide, 95 ml water, 12.5 ml ethanol, and 3.0 g 5% platinum sulfide on charcoal. The mixture is hydrogenated at 60°–65° and 500–550 psig for 2 hours. The catalyst is filtered off and washed with ethanol. The filtrate is acidified with dilute hydrochloric acid. A grey precipitate is isolated (44.5 g, 91% yield, mp 92°–94°). On recrystallization from hexane a yellow crystalline material (mp 101°–104°) is obtained which is found to be identical to the commerically available 2(2'-hydroxy-5'-tert-octyl phenyl)benzotriazole.

EXAMPLE 11

An autoclave is charged with 38 g (0.98 mole) 2,4-di-tert-amyl-6-(2'-nitrophenyl azo) phenol, 20 ml 6N sodium hydroxide, 105 ml water, 125 ml ethanol and 3.0 g 5% platinum sulfide on charcoal. The mixture is hydrogenated 1⅜ hours at 50° and 425–590 psig. The resulting crystalline compound is filtered off along with the catalyst. The product is taken up in benzene, the catalyst is filtered off and the benzene is evaporated. The residue (20.7 g; mp 78°–81°) is found to be identical to the commercial 2(3',5'-di-tert-amyl-2'-hydroxyphenyl)benzotriazole. A second crop is obtained by acidifying the original mother liquor (wt 11.7 g; mp 70–77). The combined crude yield is 92%. On recrystallization from n-hexane a pure white product (mp 78.5°–80°) is obtained.

Other alkylated hydroxy phenyl benzotriazoles can be prepared in the same fashion as in the preceding examples.

EXAMPLE 12

Into an autoclave are charged 38.5 (0.10 mole) 2(4'-choro-2'-nitrophenyl azo)-4-tert-octylphenol, 2.0 ml 6N sodium hydroxide, 110 ml water, 130 ml ethanol and 5.0 g 5% platinum sulfide on charcoal. The mixture is hydrogenated at 100° and 800–815 psig for 1½ hours. The mother liquid is acidified. The precipitate obtained is combined with the residue obtained from evaporating the benzene wash. The combined product (30 g, 83% yield) is recrystallized from n-hexane giving a 66% yield of pure (mp 90.5°–92.5°) 5-chloro-2-(2'-hydroxy-5'-tert-octylphenyl)benzotriazole. It is a nearly white crystalline substance, sufficiently soluble in such diverse solvents as hexane and ethanol to be compatible in both polar and non-polar polymers.

Examples 5 and 12 show a method for making the commercially important 5-chloro-2-(2'-hydroxy-5'-alkyl phenyl)-benzotriazoles and 5-chloro-2-(2'-hydroxy-3',5'-dialkylphenyl)-benzotriazoles. In particular the method is applicable to making 5-chloro-2-(2'-hydroxy-3',5'-di-tert-butyl phenyl)benzotriazole.

In another aspect, the invention is directed to the compound of Example 12, namely, 5-choro-2-(2'-hydroxy-5'-tert-octylphenyl)benzotriazole, which is believed to be a new chemical. This new compound is remarkably effective as a light stabilizer for polypropylene in comparison to closely related prior art benzotriazoles. Accordingly, the invention in another important aspect is directed to a composition comprising polypropylene containing the new compound 5-chloro-2-(2'-hydroxy-5'-tert-octylphenyl)benzotriazole, in amount effective to stabilize the polypropylene against deterioration by light, with or without other synthetic additives such as dialkylthiodipropionates and others (e.g., U.S. Pat. Nos. 3,134,748, 3,205,193, 3,271,339, 3,368,997, 3,405,089, 3,424,711, 3,454,412, 3,464,943, 3,477,972, 3,496,134, 3,502,613, 3,518,193, 3,549,588, and 3,598,757; further patents on the use of benzotriazoles are 3,018,269, 3,004,896, 3,211,696, 3,367,958 and 3,441,361).

In Example 13 below, the new benzotriazole stabilizer of the invention is compared, in polypropylene, to several closely related commercially available light stabilizers disclosed in U.S. Pat. Nos. 3,189,615, Heller et al., June 15, 1965 and 3,230,194, Boyle, January 18, 1966. The latter discloses 2(2'-hydroxy-5'-tert-octylphenyl)benzotriazole which differs from the chemical of the present invention only by the chlorine substituent. Yet is one examines the protective ability of the first three benzotriazoles of Example 13 one would not expect an increase in activity from the addition of a chlorine group. It is therefore very surprising to find that the addition of a chlorine group to a compound of the Boyle patent results in a 32% increase of its protective ability in polypropylene. The increase in activity over the older prior art shown in Example 13 is correspondingly greater.

The compound of this invention (i.e., the compound of Example 12) has all the usual good properties of benzotriazoles. It is compatible with the usual compounding ingredients such as antioxidants, plasticizers, etc. Besides polyolefins, it can be used in the usual polymers that benefit from benzotriazole incorporation such as polyvinylchloride, polyvinylidene chloride, polyesters, polyurethanes, polyacetals, polycarbonates, polystyrene and others. Usual levels of this stabilizer are 0.05 to 2.0%, but in exceptional cases lower (e.g., 0.01%) or more likely higher levels (e.g., 5%) can be used. The compound of this invention can be made by the usual methods of making benzotriazoles, the preferred method being reductive cyclization using hydrogen and a catalyst described in Example 12.

EXAMPLE 13

This Example is designed to show the superiority of 5-chloro-2(2'-hydroxy-5'tert-octylphenyl)-benzotriazole over commercial prior art benzotriazoles.

The benzotriazoles shown in the table below were incorporated into Profax 6501 (trademark; Hercules polypropylene) at the 0.2% level along with 0.4% dilaurylthiodipropinate by milling the resin on a mill at 330° F. Ten mil films were compression molded and exposed to a Fluoroescent Sunlight Blacklight unit. The number of days to embrittlement were noted. Also noted in the table are the added days of protection (i.e., days to embrittlement for the test chemical minus the 8 days of the blank containing no chemical).

| Benzotriazole | Days to Embrittlement | Added Days of Protection |
|---|---|---|
| None | 8 | — |
| Comparison Chemicals | | |
| 5-chloro-2(2'-hydroxy-3'tert-butyl 5'methylphenyl)benzotriazole | 28 | 20 |
| 5-chloro-2(2'-hydroxy-3',5'-di-tert-butylphenyl)benzotriazole | 70 | 62 |
| 2(2'-hydroxy-3',5'-di-tert-amyl-phenyl)benzotriazole | 65 | 57 |
| 2(2'-hydroxy-5'-tert-octyl phenyl)benzotriazole | 77 | 69 |
| Invention | | |
| 5-chloro-2(2'-hydroxy-5'-tert-octyl phenyl)benzotriazole | 99 | 91 |

I claim:

1. 5-Chloro-2-(2'-hydroxy-5'-tert-octylphenyl)benzotriazole.

2. Polypropylene containing, as a stabilizer, from 0.01 to 5% by weight of the compound recited in claim 1.

* * * * *